United States Patent [19]

Rankin

[11] 3,987,163

[45] *Oct. 19, 1976

[54] POLYSTYRENE SULFONATE CONTAINING OPTHALMIC SOLUTIONS

[75] Inventor: Billy F. Rankin, Rockville, Md.

[73] Assignee: Burton, Parsons and Company, Inc., Washington, D.C.

[ * ] Notice: The portion of the term of this patent subsequent to Sept. 23, 1992, has been disclaimed.

[22] Filed: May 1, 1975

[21] Appl. No.: 573,772

Related U.S. Application Data

[63] Continuation of Ser. No. 383,286, July 27, 1973, Pat. No. 3,907,985.

[52] U.S. Cl. ............................................. 424/78
[51] Int. Cl.$^2$ ..................................... A61K 31/74
[58] Field of Search ................................ 424/78

[56] References Cited
UNITED STATES PATENTS

| | | |
|---|---|---|
| 2,703,777 | 3/1955 | Feinstein et al. ............... 424/145 |
| 3,150,045 | 9/1964 | Boghosian ...................... 424/180 X |
| 3,183,152 | 5/1965 | Szekely et al. ................. 424/153 X |
| 3,767,788 | 10/1973 | Rankin ............................ 424/78 |
| 3,907,985 | 9/1975 | Rankin ............................ 424/78 |

OTHER PUBLICATIONS

Lofholm–"Ophthalmic Products," Handbook of Non-Prescription Drugs, pp. 99–107, (1973).
Chemical Abstracts, 54:18025a, (1960).
Chemical Abstracts, 63:2857b, (1965).

*Primary Examiner*—Leonard Schenkman
*Attorney, Agent, or Firm*—Fidelman, Wolffe & Waldron

[57] ABSTRACT

An opthalmic solution is provided for treatment of "dry eye", providing lubricating and cushioning effects for traumatized eyes, including trauma caused by the wearing of hard or gel-type contact lenses, and as a carrier for opthalmic medicaments. The solution is an aqueous solution of polystyrene sulfonate, optionally and preferably including polyethylene glycol, and other optional ingredients.

7 Claims, No Drawings

POLYSTYRENE SULFONATE CONTAINING OPTHALMIC SOLUTIONS

This is a continuation of application Ser. No. 383,286, filed July 27, 1973, now U.S. Pat. No. 3,907,985.

The present invention relates to a multi-functional opthalmic solution designed for and adapted to general use in the eyes of humans and domestic animals. The present invention further relates to the provision of a synthetic mucous layer which serves as a wetting agent in the eye, i.e. an artificial tear material useful for the treatment of both "dry eye" or as a cleaning, lubricating and cushioning agent for the eye after an injury or therapeutic surgery. The invention also relates to the utilization of the opthalmic solution as a carrier for opthalmic medicaments. Still further, the invention relates to an opthalmic solution useful as a cleaning, lubricating and cushioning agent for both hard and gel-type contact lenses. The invention also relates to the attainment of all the foregoing functions without optical interference and with a solution which may be readily buffered to any convenient pH. The invention further relates to an opthalmic solution having bactericidal activity.

Heretofore, opthalmic solutions have generally conformed to the general specifications required for all such intended utilizations in the treatment of the eye. Such solutions have generally been isotonic, buffered to the required pH, sterile and have contained additives for improved viscosity and longer retention in the eye. However, with many of such solutions, the problems of dosage, irritation to th eye, stability and occular response persist.

Many attempts have been made to resolve these problems by modifying existing formulas, using different forms of eye-treating substances, or using bases immiscible with aqueous solutions. Such attempts have added little to the performance qualities of the products.

It is accordingly an object of the present invention to provide a multipurpose opthalmic solution, suitable for general utilization in the eye of both humans and domestic animals.

A further object of the present invention is the provision of such solutions which can be readily modified for particular purposes and utilizations, including the introduction into the eye and the retention therein, of opthalmic medicaments, the provision of a wetting agent which serves as an artificial tear for the treatment of "dry eye", or a cushioning or lubricating agent for an injured or surgically treated eye, as a cleaning, lubricating and cushioning agent for utilization in conjunction with both hard and gel-type contact lenses and the like.

These and still other objects, as will become apparent from the following disclosure, are attained by the composition of the present invention which, in its broadest terms, comprises a polystyrene sulfonate polymer having a molecular weight of from about 75,000 to about 10,000,000, water, and, optionally, a polyalkylene glycol, preferably polyethylene glycol or polypropylene glycol, and having a molecular weight of about from 400 to 6,000.

Polystyrene sulfonates are known to exhibit excellent lubricating characteristics in aqueous solution and are freely soluble in water without degradation. Wide ranges of molecular weights are available. In the present invention, these can be from 75,000 up to several million, e.g. 10,000,000 or even greater. The medium molecular weight materials are preferred in the present invention and a range of 500,000 to 1,000,000 has been found particularly useful. Most preferred is a polystyrene sulfonate having a molecular weight of about 750,000. Such resins have extraordinary thickening action in water, even in the presence of salts. The thickening power increases sharply with both concentration and molecular weight. Thus, to attain the desired viscosity, substantially less polystyrene sulfonate polymer is required for a relatively higher weight that would be the case when a lower molecular weight polymer is utilized. In addition, the higher molecular weights result in a higher strength lubricating film in solutions due to orientation of polymer molecules. The concentration of the polystyrene sulfonate polymer will vary in the present invention with the molecular weight to provide a viscosity of from 0 to about 30,000 cps at 20° C. as measured by Brookfield Viscosimeter, where viscosities of from 0 to about 200 cps are measured using the ultra-low viscosity adapter rotated at a speed of 0.6 rpm, and viscosities greater than about 200 cps are measured with a number 6 spindle rotated at 10 rpm. Such viscosities will ordinarily be obtained when the concentration is within the range of about 0.05 to 20.0 weight percent, often preferably about 0.1 to 5.0 weight percent, depending upon the molecular weight of the polymer employed. With lower viscosities (whether due to lower molecular weight polymers or lower concentration, or both) inferior lubrication results. Higher viscosities result in difficult handling properties and characteristics, including insufficient flowability for fully effective utilization in the eye.

As used in the present disclosure, the term "polystyrene sulfonate" is intended as a convenient term to denote the class of polymers which is characterized by the polymerization of alkenyl aromatic sulfonates or the sulfonation of polymers of alkenyl aromatics and, as such, is not limited to the literal polystyrene sulfonates, but is also inclusive of copolymers of styrene sulfonate and both homopolymers and copolymers of styrene sulfonate analogs as well. It is also intended that the wide variety of polymers produced by sulfonation of alkenyl aromatic containing polymers be included as well.

The polystyrene sulfonate polymers as thus defined are a well known class of polymers, many variations of which are commercially available. The polymerization techniques for the preparation of such materials are similarly well known to those of ordinary skill in the art and many variations of such techniques are similarly in practice in commerce.

The water soluble, linear, high molecular weight polymer sulfonates with which this invention is concerned correspond to addition polymers of monoalkenylaromatic sulfonates having the formula:

wherein Ar is a divalent aromatic radical selected from the group consisting of hydrocarbon radicals and nuclear chlorinated hydrocarbon radicals having its valence bonds on nuclear carbon atoms, R is a member of the group consisting of hydrogen and methyl, M is a cation and the other symbols have their usual meanings.

Specific examples of sulfonates which are used in accordance with this invention are water-soluble, linear, high molecular weight polymers of styrenesulfonic acids, α-methylstyrenesulfonic acids, ar-methylstyrenesulfonic acids, ar-dimethylstyrenesulfonic acids, α,ar-dimethylstyrenesulfonic acids, ar-ethylstyrenesulfonic acids, ar-isopropylstyrenesulfonic acids, vinylnaphthalenesulfonic acids, ar-chlorostyrenesulfonic acids, ar-dichlorostyrenesulfonic acids, ar-chloro-ar-methylstyrenesulfonic acids, and the water soluble salts of such resin sulfonic acids.

The term "sulfonate" is used herein to mean the free sulfonic acid and its salts. M in the foregoing formula being a cation, including hydrogen and metal, ammonium, amine and like salt-forming cations. Specific examples, for purpose of illustration and not of limitation, of suitable salts are the sodium, calcium, potassium, ammonium and amine salts of the polymer sulfonates.

The addition polymers correspond to homopolymers of the monoalkenylaromatic sulfonates, copolymers of two or more such sulfonates and one or more of other monoethylenically unsaturated monomers wherein the monoalkenylaromatic sulfonate is at least 60 percent by weight of the total polymer. In the latter such polymers, units corresponding to a monoalkenylaromatic sulfonate are are additionally combined with units corresponding to one or more kinds of monoethylenically unsaturated compounds, examples of which, for purposes of illustration and not of limitation, are styrene, -methylstyrene, ar-methylstyrenes, ar-dimethylstyrenes, ar-dimethylstyrenes, ar-ethylstyrenes, ar-isopropylstyrenes, vinylnaphthalenes, ar-chlorostyrenes, ar-dichlorostyrenes, ar-chloro-ar-methylstyrenes, isobutylene, ethylenically unsaturated esters, e.g. 1–12 carbon atom alkyl esters of acrylic or methacrylic acids, vinyl esters of fatty acids such as vinyl acetate, vinyl chloride, vinylidene chloride, methyl isopropenyl ketone, methyl vinyl ether, and acrylonitrile.

The term "water soluble" is used herein to mean that the polymer sulfonates form true solutions in pure water, which solutions are free of gel particles and infinitely dilutable with water.

By the term "linear", it is meant that the polymeric chain is free or nearly free of crosslinkages. A water soluble polymer sulfonate is regarded as linear for practical purposes of this invention if its water solution is free of gels, infinitely dilutable with water, and filterable through ordinary filter paper (Whatman's Number 1) without loss of viscosity.

The water soluble, linear, high molecular weight polymer sulfonates for use in this invention are obtained either by polymerization of the corresponding monoethylenically unsaturated monomers including a monoalkenylaromatic sulfonate or by sulfonation of a starting polymer of monoethylenically unsaturated monomers including a polymerically combined monoalkenylaromatic hydrocarbon or nuclear chlorinated monoalkenylaromatic hydrocarbon.

When the polymer sulfonates are obtained by sulfonation of a monoalkenylaromatic polymer resin, the resin starting material is a toluene-soluble, thermoplastic, linear, high molecular weight addition polymer of a monoalkenyl aromatic hydrocarbon or nuclear chlorinated monoalkenylaromatic hydrocarbon having the general formula:

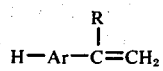

wherein H - Ar is a monovalent aromatic hydrocarbon or nuclear chlorinated hydrocarbon radical having its valence bond on a carbon atom of a sulfonatable aromatic nucleus, R is hydrogen or a methyl radical, and the other symbols have their usual meanings. By "sulfonatable", it is meant that the nucleus of the aromatic radical has at least one hydrogen atom replaceable by the sulfonic acid group by reaction with sulfonation agents such as sulfuric acid and sulfur trioxide.

Examples of such monoalkenylaromatic polymers are the solid homopolymers of styrene, αmethylstyrene, ar-methylstyrenes (ar-vinyltoluenes), ar-dimethylstyrenes, α,ar-dimethylstyrenes, ar-ethylstyrenes, vinylnaphthalenes, and ar-chlorostyrenes; copolymers of two or more of such monoalkenylaromatic compounds, e.g. copolymers of styrene and ar-vinyltoluene and copolymers of styrene and α-methylstyrene; and copolymers of a major proportion of one or more of such monoalkenylaromatic compounds such as monoethylenically unsaturated hydrocarbons, e.g. isobutylene, monoethylenically unsaturated esters, e.g. 1-12 carbon atom alkyl esters of acrylic or methacrylic acid, and acrylonitrile.

When the polymer sulfonates for use in this invention are made by sulfonation of monoalkenylaromatic hydrocarbon or other nuclear chlorinated hydrocarbons, the starting polymers are further characterized as being linear, i.e. free of crosslinkages and having high molecular weight. Moreover, it is necessary that the means and method of sulfonation of the starting monoalkenylaromatic polymers be such that the resulting polymer sulfonates are water soluble, linear, high molecular weight products.

Methods are already known per se for making polymer sulfonates conforming to the above-described characteristics. However, it will be understood by those skilled in the art that methods of making polymer sulfonites do not invariably produce products having the characteristics set forth above. It is the polymer sulfonate that it controlling in the present invention and not the procedure by which it is prepared.

Aqueous solutions of the polystyrene sulfonate resins have a low level of oral toxicity and an extreme level of compatibility in contact with the skin or in the eye. They are also characterized by a high level of pituitousness and an extraordinarily high degree of pseudo-plasticity. The solutions are highly stable through a wide range of temperatures and can tolerate extremely wide variations in pH.

Because of the strong ionic bonding affinity of the sulfonate group in the polystyrene sulfonate chain, the resin solutions will form ionic salts and association complexes with a wide variety of materials. Such ionic salts association complexes per se often exhibit properties markedly different from either component alone, but it has been found that the resin will give up associated materials when introduced into the eye. The dissociation in vivo may result from an ionization effect produced by the materials with which the solutions are contacted, e.g., various salts occuring in tears and the like.

Because of the high levels of pseudo-plasticity and pituitousness of polystyrene sulfonate aqueous solutions, it is highly desirable to include in the solution a material which will render a plasticizing effect. In addition, it is also desirable to include a humectant which will enhance fluid retention over the course of long term usage in the eye. These functions are provided by the inclusion in the solution of a polyalkylene glycol. The preferred polyalkylene glycol is polyethylene glycol, such as the Carbowaxes, as supplied by Carbide and Carbon Chemicals Company. Such materials have molecular weights ranging from about 400 up to as much as about 6000. Particularly preferred in the compositions of the preferred invention is polyethylene glycol having molecular weight of about 4000, although this preference is primarily because of the ready availability and convenience of processing of the particular material. Polyglycols containing other alkylene groups can be utilized, such as polypropylene glycols and the like, but such materials are often not as readily available, and for this reason alone are not particularly preferred in the present invention. The polyalkylene glycol can be present in amounts ranging up to 5000, preferably 500 to 5000, weight percent based on the weight of the polystyrene sulfonate polymer. Less than about 100% by weight can occasionally result in insufficient water retention and plasticizing effect, with concomittent drying of the eye and irritation of occular tissue, while amounts greater than about 5000 weight percent can exhibit a "salting out" effect, with the formation of waxy solid globules or particles which can be irritating to occular tissues.

The basic opthalmic solution of the present invention, i.e. the aqueous solution of polystyrene sulfonate and polyalkylene glycol, is useful per se in a number of contexts. Primary among these is the provision of a synthetic mucous layer, which serves to clean and lubricate the eye, serving as a wetting agent and artificial tear for the treatment of dry eye or to provide a cushioning and lubricating effect in an injured or surgically treated eye. A related effect is the cleaning, lubricating and cushioning effects attained when the solution of the present invention is used in conjunction with contact lenses, of both the hard resin and gel type. Representative of the problems generally applicable to each of the foregoing usages is the use of the opthalmic base solution of the present invention in conjunction with gel-type contact lenses, and accordingly, the use of the solution will be discussed with particular reference thereto.

The advent of the gel contact lens has generated entirely new requirements for contact lens treating solutions and entirely new problems in hygenic handling and care for the lenses. In contrast to the more common hard type lens, usually made of polymethylmethacrylate, the gel lens will absorb relatively large proportions of water to form a soft, pliable material which has a tendency to fray. The gel is a three-dimensional lattice formed by the polymerization of glycol esters and diesters of acrylic acids. The glycol moieties of the molecules imparts a strong hydrophilic character to the lattice, with the consequent ability to absorb rather large amounts of water. By utilizing the unique properties of these lenses, new therapeutic options are presented for the treatment of occular debilities. Since the lens per se represents only the environment of use of the composition, a more complete discussion of its physical parameters need not be repeated here. A discussion of the gel contact lens, including both the preparation and use thereof occurs in Augenoptika, Heft 6, 1965, pages 5 and 6, Vienna, Austria, which reports a paper delivered by Maximillian Dreyfus at the 15th WVA annual meeting.

One characteristic peculiar to the gel lens is the requirement that treating solutions contain no component that can become entrained in the lattice of the gel, since such materials tend to accumulate and become irritating to the occular tissue. The lens does, however, require a cleaning and lubricating solution to cushion the occular tissue from direct contact with the lens. The requirement for a cleaning action is shared by the gel-type lens with hard lenses and with synthetic tears and other such opthalmic solutions. The exposure of the eye to various atmospheric pollutants, such as smoke, dust, pollen, noxious and irritating gases and the like can create severe discomfort and irritation, particularly in situations where the pollutants collect in the natural or artificial tear film to persist for materials must be compatible with the gel and with occular tissue and not interfere with the physio-chemical balance of the precorneal films.

The attainment of these objectives is illustrated by the following example.

EXAMPLE I

A polystyrene sulfonate polymer having a molecular weight of about 75,000 (National Starches & Chemical Corp. Versa-TL 70) and polyethylene glycol having a molecular weight of about 4,000 (Carbowax 4000) are dissolved in distilled water in the following proportions:

| Polyethylene glycol | Polystyrene sulfonate | Distilled water |
| --- | --- | --- |
| 9.00 gms | 0.30 gms | 300.00 ml |

The solution is utilized to clean and hydrate gel-type contact lenses by immersing each lens in sufficient of the solution to completely cover the lens. Full hydration is effected in about 1–10 minutes. At the end of the immersion, the lens is lightly rubbed between the fingers and rinsed with water. Each lens is examined and was found to be fully hydrated and optically clear. The lenses are then implaced in human eyes in conventional fashion and are left in place for periods of 12 to 17 hours without noticeable irritation. In dry environments or drafts, some subjects / flush the lenses while in place with small increments of the solution (which is found to effectively clean and rehydrate the lenses), whereby the tolerance period of the subject is enhanced and any drying problem alleviated.

By comparison, conventional lens wetting solutions of types commercially available are found to provide inferior cleaning and the ingredients occlude in the lens and cause irritation of the occular tissues.

In addition to the foregoing tests, both the solution of the present invention and the commercially available lens solution of U.S. Pat. No. 3,171,752 were tested for retention in the eye in the following fashion A minor amount of florescein dye was incorporated into each solution. One solution was placed in one eye, the other solution in the other eye, of a number of rabbits. Examination of the eyes using an ultra-violet light source gave a quantitative base measure of the amount of solution present. Periodic repetitions of the examination revealed that this solution was gradually lost in either case, but that the commercial solution was retained much less effectively. The eyes treated with the solution of this example retained at one and one-half hours the same amount of solution as did the eyes treated with the commercial solution at twenty-five minutes. Details of the fluorophotometric determination can be found in Waltman et al, *Investigative Opthalmology*, Vol. 9, No. 4, pp. 247–249, April, 1970.

In no case, including both the utilization of the gel-type contact lens in the human eye or the solution alone in the eyes of test rabbits, was any evidence or irritation of the eye found to result from the solution of the present example.

In addition to the per se usefulness of the opthalmic solution of the present invention as illustrated in the foregoing Example 1, the opthalmic solution of the present invention finds an additional area of broad utility as a carrier for opthalmic treating materials such as medicaments (particularly those requiring an acid pH). The high effectiveness of the opthalmic solution of the present invention is believed due to the strong ionic bonding affinity of the sulfonate group of the polystyrene sulfonate chain. When combined with the opthalmic solution of the present invention, opthalmic medicaments are found to exhibit a much greater retention on orbital tissue and results in a longer duration of medicament activity. In addition, the degree of retention attained permits the use of smaller amounts of the eye treating substances than has been found heretofore possible while maintaining the necessary levels of effectiveness. Examples of medicaments with which the carrier can be used are:

Pilocarpine, HCL
Hydrocortisone USP (alcohol)
Hydrocortisone Acetate
Prednisolone Acetate and other cortisones
Neomycin Sulfate
Bacitracin
Penicillin
Sulfamerazine
Sodium sulfacetamide
Sulfadiazine
Sulfasoxozone and other sulfa derivatives
Scopolamine hydrobromide
Epinephrine bitrartrate
Phenylephrine HCl or other derivatives
Prostigmin bromide
Pilocarpine (any of the salts)
Idoxuridine
Antipyrine
Naphthazoline HCl
Antazoline phosphate The foregoing list is intended to be merely exemplary. As the list illustrates, the opthalmic solution of the present invention can be utilized as a carrier for substances such as antibiotics, mydriatics, biotics, antihistamines, and the like. The amount of eye treating substances used with the composition of the present invention depends upon the nature of this substance or substances employed and the response of the individual receiving treatment. Typically, up to 500% or even more, based on the weight of the polyethylene oxide, of the eye treatment medicament can be used.

When the eye treating substance or substances are those requiring an acid pH, one or more acids can be present in amounts sufficient to maintain the solutions at a pH of less than 7 and as low as about 3. An example of an acid which can be used with eye treating substances such as medicaments requiring an acid pH is boric acid. However, many eye treating substances must be maintained in a basic or neutral medium. In these instances, one or more pH buffers such as sodium borate is added to maintain a solution of a neutral or slightly basic pH. Typically, the buffering substances present in an amount sufficient to maintain the pH at the desired level are from between about 7.4 and about 8.2, and preferably at about 7.6. Other buffering compositions can be used as well, including a combination of phosphates such as, for example, monosodium phosphate and disodium phosphate to provide both acid and base control. Other phosphates, acetates and carbonates can be substituted for the phosphates mentioned above - provided they are compatible with the eye. Specifically, the amount of buffering additions can range from about 0 to 4%, preferably about 0.2% for the dibasic component, and from about 0 to about 0.5% for the mono-basic component, wherein the percentages are by weight based upon the total weight of the overall composition, with the ratio of components balanced to provide proper pH for the overall composition.

The utilization of the opthalmic solution of the present invention as the carrier for the opthalmic medicaments is illustrated by the following example

EXAMPLE II

The following composition is illustrative of the utilization of the composition of the present invention as a carrier for medicaments: a polystyrene sulfonate polymer having a molecular weight of about 700,000 (National Starches & Chemical Corp. Versa-TL-700), and a polyethylene glycol having a molecular weight of about 4,000 (Carbowax 4000) are dissolved in distilled water in the following proportions:

| | |
|---|---|
| Polystyrene sulfonate | 9.00 gm |
| Ethylene oxide polymer | 0.30 gms |
| Distilled Water | 300.00 ml |

To the base solution, there are then added 6.00 gm of pilocarpine HCl and 3.00 gm of boric acid. Both the salt and the acid dissolve readily in this solution.

The foregoing formulation is utilized in the treatment of glaucoma patients who had previously required four standard pilocarpine treatments per day. It is found that three treatments with the formulation of the present invention provides the same therapeutic effects as the four standard treatments. Studies on normal eyes of both animals and humans, after the fashion indicated in Example I, showed no adverse effects after prolonged application periods, and a much longer period of retention in the eye for each application.

Whatever the contemplated utilization of the opthalmic solution of the present invention, it can be desirable to include in the solution one or more of a variety of secondary additives as hereinafter described in fuller detail. For example:

Highly compatible cellulose derivatives of a variety soluble in water, such as for example, methyl cellulose, hydroxyethyl cellulose, carboxymethyl cellulose, hydroxypropyl methyl cellulose and the like, can be included in the solution to act as a mechanical buffer or as a viscosity control agent. These can also be used to maintain the viscosity of the overall composition within the desired range as hereinbefore described. Specifically, the cellulose derivatives when employed should be present in an amount sufficient to maintain viscosity of the overall composition at the desired level.

The composition of the invention can also contain one or more eye compatible biocides, such as thimerosal (sodium ethylmercurithiosalicylate), and the di-, tri-, or tetradosium ethylenediamine tetraacetates. The percentages of such biocides can vary over a broad range, but typically do not exceed about 1% by weight of the overall composition.

In addition, the composition of the present invention can also contain one or more eye compatible non-ionic surfactants in amounts varying over a wide range (but typically in amounts up to about 0.5% by weight) in order to provide product stability. An example of the surfactants which can be utilized are Tergitol 1559 (Carbide and Carbon Chemicals Co.); Pluronic F68 (Wyandotte Chemical Corp., Michigan Alkali Division); Tweens of H.L.B. value of 11 or higher (Atlas Powder Company).

Still another subsidiary component which can be added to the opthalmic solutions of the present invention includes polyvinyl pyrrolidone (such as Plasdone C, supplied by Entira Chemicals, division of GAF Corp.) which performs a number of desirable functions. Polyvinyl pyrrolidone (PVP) acts as a detoxicant, binding anti-toxins present in eye fluids and rendering them harmless. PVP also acts to protect the solution by preventing its breakdown because of particle agglomeration and acts as a demulcent lubricant by a combination of adhesive and lubricating properties which aid in the spreading of the viscous solution. The PVP also operates to prevent blepharospasm (involuntary eyelid contraction), but has little effect on an overall composition viscosity. PVP is desirably present in an amount of from 0.5 to 10.0 weight percent based on the overall solution.

The foregoing illustrations of secondary additives for the opthalmic solution of the present invention are intended to be merely exemplary of the more common of the additives to opthalmic solutions well known to those of ordinary skill in the art. It should accordingly be understood that such additives are not required for effective operation of the opthalmic solution of the present invention, nor is it intended by the enumeration of certain additives to exclude others.

While the opthalmic solution of the present invention is readily formed by simply combining the ingredients, the polystyrene sulfonate material can occasionally present difficulties in readily dissolving due to the formation of lumps. Such difficulties can be avoided by the utilization of the following technique; an increment of distilled water sufficient to dissolve the constituents of the composition is placed in a stainless steel container and heated to about 50° C. If a surfactant is included in a composition, it is dissolved first in distilled water by agitation, e.g. with a dispersing mixer which has a variable speed control set at a low speed.

Any medicament (such as pilocarpine HCl, pH buffers) and the polyalkylene glycol (such as Carbowax 4000) and other additives (such as biocides and the like) are then dissolved with medium speed agitation in the water/surfactant mixture, following which the polyvinyl pyrrolidone is added with high-speed mixing and agitation. If a cellulosic derivative mechanical buffer is utilized, it is sifted slowly into the vortex created by the agitator at high speed. When the cellulosic substance is completely dispersed, the polystyrene sulfonate is sifted slowly into the vortex at high agitation, until the resin appears to be climbing up the agitator shaft, at which time the speed is reduced to 100 to 200 rpms. Agitation is then continued until the resin is completely dissolved in the solution, typically from 2 to 6 hours. Additional distilled water is then added to bring the solution up to volume. When some components are temperature sensitive, the product may be sterilized after packaging by means of ethylene oxide gas sterilization. Containers for the solution are placed in racks in a gas autoclave, which draws a vacuum of about 24 ml of mercury, after which all air is replaced with an ethylene oxide-freon mixture (12-88%) at 12 psi for 12 hours and at relative humidity of 45 to 50%. It is also possible to sterilize in an autoclave if the conditions are controlled to minimize thermal damage to any sensitive ingredients.

EXAMPLE III

As an illustration of the composition of the present invention containing the aforementioned secondary additives, the following composition was prepared on a relatively large scale:

| | | |
|---|---|---|
| bacteriocide (Thimerosal, 10%) | 240 | cc |
| disodium phosphate | 1200 | gms |
| polyethylene glycol (MW. 4,000) | 6000 | gms |
| polyvinyl pyrrolidone | 3000 | gms |
| disodium ethylenediamine-tetracetate | 600 | gms |
| non-ionic surfactant | 132 | gms |
| hydroxy ethyl cellulose (MW 52,000) | 3000 | gms |
| polystyrene sulfonate (Versa-TL-700) | 3000 | gms |
| distilled water | 150 | gallons |

The solution formed from the foregoing components was clear and free of polymer globules and was found to have a pH of about 7.3 and a viscosity of about 150 cps.

The solution was utilized as a wetting, cleaning and cushioning medium by a number of pateints using hard-type, polymethyl methacrylate contact lenses. With patients who had previously worn the lenses, greater comfort and tolerance were reported, even by those who had previously experienced difficulty with the lenses. Most patients reported that they were able to wear their lenses for greater periods of time than had previously been possible, regardless of the type of wetting solution they had used before. With patients who had not previously worn contact lenses, the solution of the present invention dramatically reduced the problems of lens delivery and greatly accelerated the adaptation of the patients to the use of the lenses. In all the trials, no adverse side effects or irritation was noted either subjectively or by clinical examination.

It has been noted that in the utilization of the opthalmic solution of the present invention with contact lenses, certain ranges of viscosity provide better results than others. For example, with hard-type lenses, the best results are attained at a viscosity of about 30 to 200 cps and that range is accordingly preferred for such usage. The most preferred viscosity for use with hard-type lenses is about 150 cps. With the gel-type lens, the most effective (and hence the preferred) viscosities lie in the range of about 0 to 30 cps, with values of about 10 being most preferred. No variation of effectiveness with viscosity has been noted when the solution is used as a carrier for medicaments or as a synthetic tear or the like.

It should be noted that a viscosity of zero as measured is a result of the limitations of the available techniques and apparatus and does not represent such an anomaly as it might superficially appear. It should be further noted that all designations of viscosity appearing herein represent the values as obtained with the Brookfield Viscosimeter where all values below 200 are obtained with the ultra-low viscosity adapter rotated at 0.6 rpm and all values above 200 are obtained with a number 6 spindle at 10 rpm. For values ranging from about 175 to 250 cps, results obtained by the two differing adaptations are generally comparable in the case of the present solutions.

A further example of the effectiveness of the composition of the present invention occurs primarily in the area of ophthamologic diagnosis, where it is conventional to apply fluorescein or a comparable material, dissolved in a carrier, to the eye. After allowing the dye to penetrate the tissues of the eye, an examination is conducted by visual inspection with the aid of an ultraviolet light source, which causes the dye to flouresce. It has been found that when the opthalmic solution of the present invention is utilized as the carrier, the dye is absorbed in substantially greater proportions and at a much faster rate than has been possible with the compositions of the prior art. Accordingly, solutions of fluorescent dyes in the opthalmic solution of the present invention are of great aid in the examination of the eye.

While certain specific considerations have been disclosed and discussed herein, such have been offered solely to exemplify the present invention and should in no way be construed as limiting. The proper scope and nature of the invention is set forth in the following claims.

What is claimed is:

1. An opthalmic solution comprising an aqueous solution of a styrene sulfonate polymer having a molecular weight of about 75,000 to about 10,000,000 in an amout of from about 0.05 to 20 weight percent sufficient to provide a viscosity of from about 0 to 30,000 cps. and a material selected from the group consisting of (1) acids in an amount to maintain the pH of the solution at less than 7, the said acid-containing solution being compatible with the eye and (2) eye compatible buffers in an amount sufficient to maintain the pH of the solution at from about 7.4 to about 8.2

2. The composition of claim 1 wherein said material is boric acid.

3. The composition of claim 1 wherein said buffer is a combination of monosodium and disodium phosphates.

4. The composition of claim 1 wherein said aqueous solution further includes a mechanical buffer selected from the group consisting of methyl cellulose, hydroxyethyl cellulose, hydroxypropyl cellulose, carboxymethyl cellulose, hydroxypropyl methyl cellulose, and mixtures thereof.

5. The composition of claim 1 wherein said aqueous solution further includes up to about 0.5% by weight of an eye compatible non-ionic surfactant.

6. The composition of claim 1 wherein said aqueous solution further includes up to about 5% by weight polyvinyl pyrrolidone.

7. A method of treating the human or non-human animal eye to provide a synthetic mucous layer to serve as a wetting, cleaning, lubricating and cushioning agent, which comprises adding thereto an effective amount of an opthalmic solution comprising an aqueous solution of a styrene sulfonate polymer, having a molecular weight of about 75,000 to about 10,000,000 in an amount from about .05 to 20 weight percent sufficient to provide a viscosity of from about 0 to 30,000 cps.

* * * * *